United States Patent [19]

Takeuchi et al.

[11] Patent Number: 4,758,660
[45] Date of Patent: Jul. 19, 1988

[54] CRYSTALLINE ERLOSE

[75] Inventors: Kanou Takeuchi; Shuzo Sakai; Toshio Miyake, all of Okayama, Japan

[73] Assignee: Kabushiki Kaisha Hayashibara Seibutsu Kagaku Kenkyuju, Okayama, Japan

[21] Appl. No.: 786,823

[22] Filed: Oct. 11, 1985

[30] Foreign Application Priority Data

Oct. 24, 1984 [JP] Japan .................. 59-223378

[51] Int. Cl.$^4$ .......... C07H 1/00; C07H 3/00; C07H 1/06; C07G 17/00
[52] U.S. Cl. ................... 536/1.1; 536/123; 536/124; 536/127
[58] Field of Search ............ 536/1.1, 123, 124, 127

[56] References Cited

U.S. PATENT DOCUMENTS

| | | | |
|---|---|---|---|
| 3,646,006 | 2/1972 | Lord | 536/124 |
| 4,199,373 | 4/1980 | Dwivedi et al. | 127/60 |
| 4,199,374 | 4/1980 | Dwivedi et al. | 127/60 |
| 4,652,640 | 3/1987 | Sakai et al. | 536/124 |

FOREIGN PATENT DOCUMENTS

| | | | |
|---|---|---|---|
| 0039123 | 4/1981 | European Pat. Off. | |
| 1389856 | 4/1975 | United Kingdom | |
| 2097004 | 10/1982 | United Kingdom | 536/127 |
| 2155934 | 10/1985 | United Kingdom | |

OTHER PUBLICATIONS

Hassid, W. et al., "Oligosaccharides", pp. 515–518, in *The Carbohydrates*, edited by W. Pigman, (1957).
Kirk–Othmer, *Encyclopedia of Chemical Technology*, vol. 6, (1965), pp. 482–515.
White et al., "-Maltosyl -Fructofuranoside, a Trisaccharide Enzymically Synthesized from Fructose", *J.A.C.S.*, vol. 75, 1953, pp. 1259, 1260.
Stodola et al., "The Preparation, Properties and Structure of the Disaccharide Leucrose", *J. Amer. Chem. Soc.*, vol. 78, 1956, pp. 2514–2518.
Siddiqui et al., "Isolation and Characterization of Oligosaccharides from Honey", *J. Agr. Res.*, (7) 1:51–59, (1968).
Yamada et al., "Evaluation of Cariogenicity of Glycosylsucrose by a New Method to Measure pH under Human Dental Plaque in situ", *J. Dental Res.*, vol. 59, (1980), pp. 2152–2162.
Yamada et al., "Metabolism of Glucosylsucrose and Maltosylsucrose by *Streptococcus mutans*", *Caries Research*, 14: 239–247, (1980).
Mizuno et al., "Hydrolysis of Glucosyl–Sucrose and Maltosyl–Sucrose by Rat Intestinal Disacchridases", *J. Jap. Soc. of Food and Nutrition*, vol. 33, 3, 1980, pp. 193–195.
Yamada et al., "Hydrolysis of Glucosyl–Sucrose and Maltosyl–Sucrose by Rat Intestinal Disaccharidases", *J. of Jap. Soc. of Food and Nutrition*, vol. 34, 2, 1981, pp. 133–138.

Primary Examiner—Ronald W. Griffin
Assistant Examiner—Nancy S. Carson
Attorney, Agent, or Firm—Browdy and Neimark

[57] ABSTRACT

Disclosed are hitherto-unknown erlose hydrate, a mixture solid containing the same, and their production and uses. One mole of the erlose hydrate has 1 or 3 moles of cystallization water. The erlose hydrate and a mixture solid containing the same are readily dissolvable in water, non- or scarcely-hygroscopic, low-cariogenic, low-calorific, and, therefore, favorably usable to prepare orally-usable products, e.g. foodstuffs in general, cosmetics, dentifrices, pharmaceuticals, and chemicals.

4 Claims, 5 Drawing Sheets

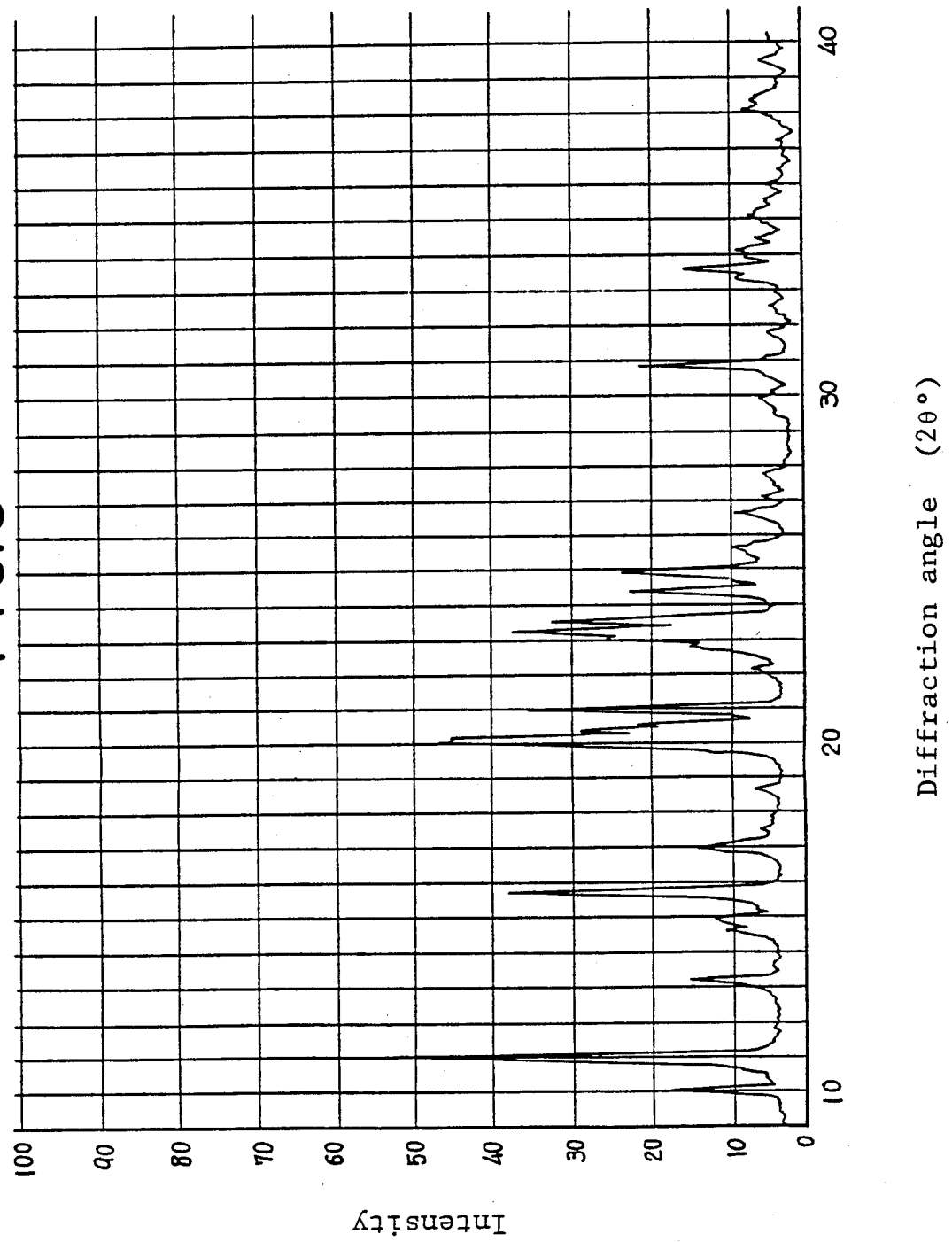

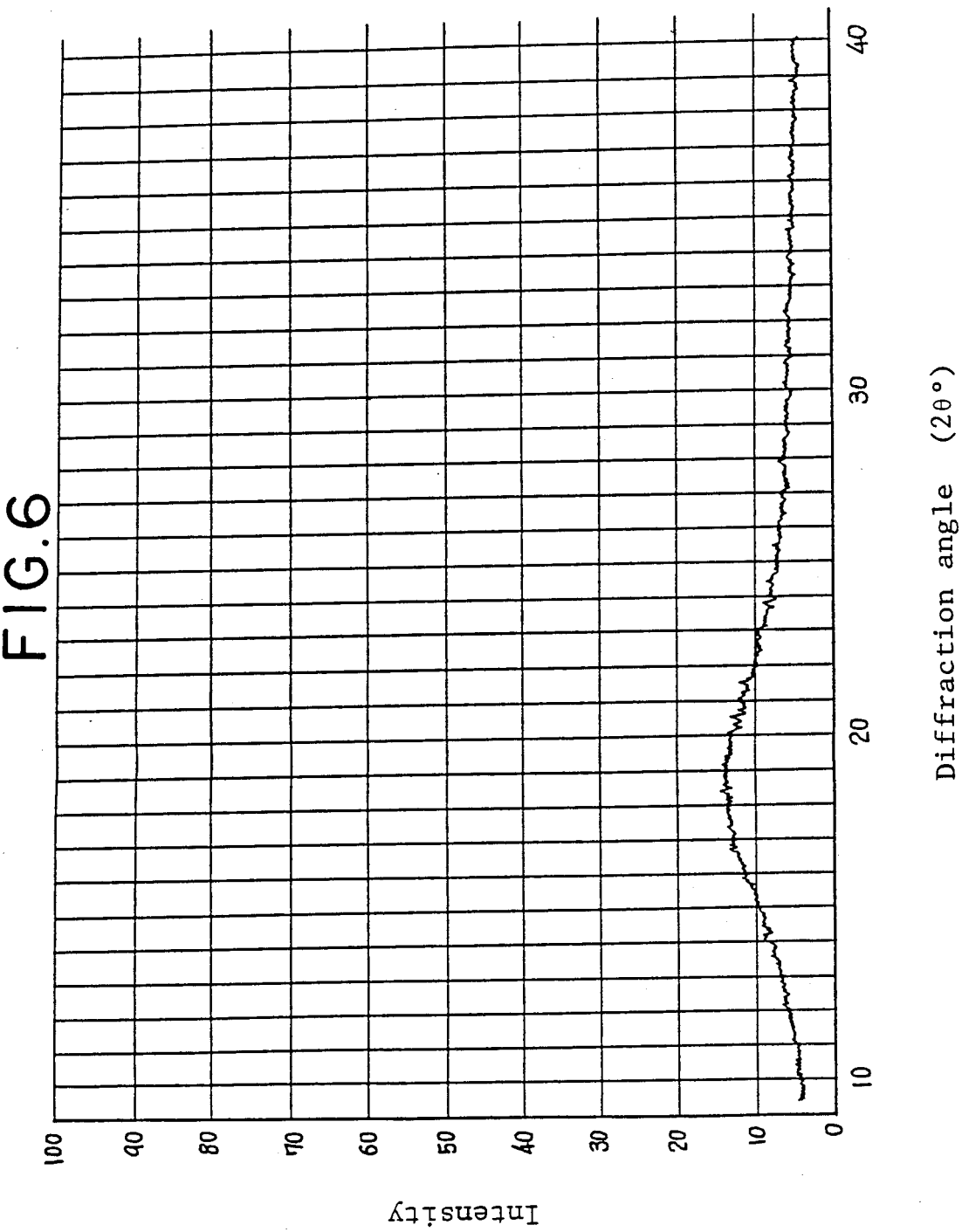

1

CRYSTALLINE ERLOSE

FIELD OF THE INVENTION

The present invention relates to crystalline erlose, in particular, crystalline erlose hydrate, mixture solid containing the same, and their production and uses.

DEFINITIONS

Percentages are given by weight on dry solid basis, unless specified otherwise.

All parts are given by weight.

Saccharide L designates a saccharide or a saccharide mixture with a degree of polymerization of 4 or higher.

Saccharide S designates a saccharide or a saccharide mixture with a degree of polymerization degree of 2 or lower.

DESCRIPTION OF THE PRIOR ART

Erlose, a trisaccharide with a structural formula of α-maltosyl β-D-fructofuranoside or $4^G$-α-D-glucopyranosyl sucrose, is known as one sweet component of honey and "Coupling Sugar ®", a glycosyl sucrose commercialized by Hayashibara Co., Ltd., Okayama, Japan.

As described in *Caries Research,* Vol.14, pp. 239–247 (1980) and *Journal of Dental Research,* Vol.59, pp.2152–2162 (1980), erlose has a taste quality close to that of sucrose, and is also known as a low-cariogenic saccharide which forms, unlike sucrose, less dental deposit and acids. In addition, *Journal of Japanese Society of Food and Nutrition,* Vol.33, No.3, pp.193–195 (1980), and ibid., Vol.34, No.2, pp. 133–137 (1981) describe that erlose is, as in the case of sucrose or maltose, hydrolyzed by intestinal mucosal dissaccharide hydrolase. Thus, the use of erlose as a new-type sweetener is in great expectation.

As evident from *Journal of the American Chemical Society,* Vol.75, pp. 1259–1260 (1953), or *Journal of Apicultural Research,* Vol.7, No.1, pp. 51–59 (1968), erlose is, however, very unwieldy because it is an amophous and hygroscopic saccharide.

So far erlose is available only in an unwieldy, amorphous, hygroscopic, pulverulent form, but no improvement to overcome these disadvantages has been attempted.

BRIEF DESCRIPTION OF THE DRAWINGS

FIG. 5 is an x-ray diffraction figure of crystalline erlose II.

FIG. 6 is an x-ray diffraction figure of an amorphous erlose used as the control.

DETAILED DESCRIPTION OF THE INVENTION

Figure 1:
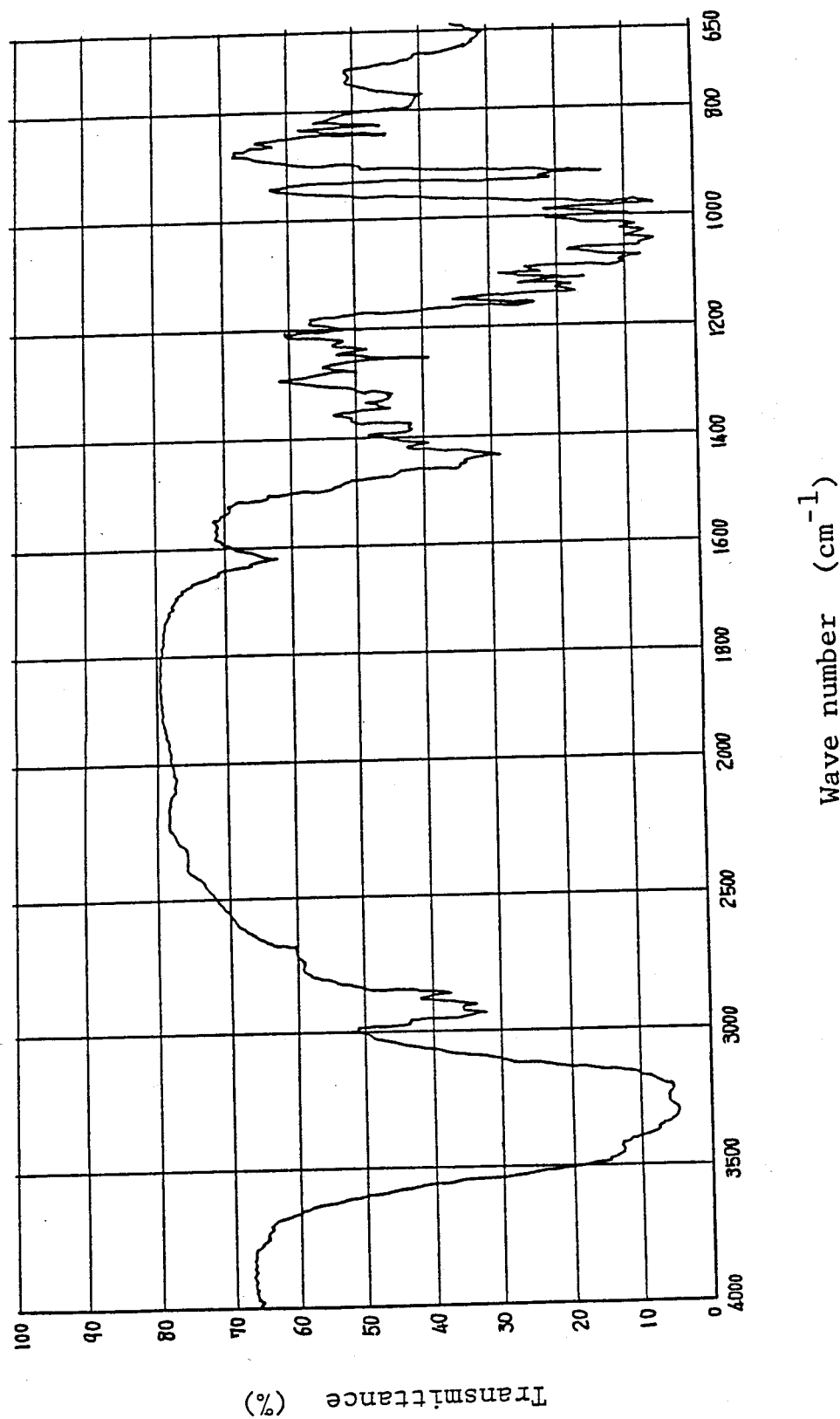
FIG. 1 is an infrared spectrum of crystalline erloses I and II.

The present inventors investigated non- or scarcely-hygroscopic crystalline erlose and its production.

As the result, a crystal was obtained by subjecting a solution containing β-cyclodextrin and sucrose to the action of cyclomaltodextrin glucanotransferase (EC 2.4.1.19), fractionating the resultant mixture solution containing erlose with a column of a strongly-acidic cation exchange resin in an alkaline-earth metal form, recovering a fraction with an erlose purity of 95%, and purifying and concentrating the fraction into about 78% syrup, placing the resultant syrup in a glass beaker, and allowing the syrup to stand at 10°–25° C. over a period of about three months.

A 70% syrup of the above fraction was seeded with the crystal, and then gradually cooled while accelerating crystallization by gentle stirring. The crystal, separated from the resultant crystal suspension, was washed by spraying a small amount of water, dissolved in water, and recrystallized by treating as above. The resultant crystal was separated from the crystal suspension, and dehydrated by a two-day ventilation at ambient temperature. Thus, a high-purity crystalline erlose (designated as "crystalline erlose I") was obtained.

A portion of crystalline erlose I was placed in a glass beaker, added with about ten volumes of methanol, dissolved by heating, cooled, and allowed to stand at ambient temperature for three days. Thus, a crystal was newly formed. A liquid obtained by melting crystalline erlose I at about 100° C. was seeded with the crystal, and crystallized into block by allowing the liquid to stand at about 60° C. for eight hours. The block was then pulverized, and dehydrated in an air stream at ambient temperature for about five hours to obtain a crystalline erlose (designated as "crystalline erlose II").

Physicochemical studies on these crystalline erloses I and II revealed that they were novel non-hygroscopic crystalline erloses, more particularly, crystalline erlose hydrates. Thus, we accomplished the present invention.

The physicochemical properties of the crystalline erloses will be described hereinafter.

(1) Elemental analysis (as anhydrous solid): Found: C=42.1%, H=6.8%, O=51.1% for crystalline erlose I; and C=42.3%, H=6.7%, O=51.0% for crystalline erlose II. Calculated: C=42.85%, H=6.41%, O=50.74%.

(2) Molecular weight (as anhydrous solid): 504.5 for crystalline erloses I and II.

(3) Moisture content (as determined by the Karl Fischer method): 9.7% for crystalline erlose I (3 moles of crystallization water/mole). 3.4% for crystalline erlose II (1 mole of crystallization water/mole).

(4) Melting point: 80.0°–80.5° C. for crystalline erlose I. 136.5°–137.0° C. for crystalline erlose II.

(5) Specific rotary power $[\alpha]_D^{25}$ (in 1% aqueous solution); Plus 112.0 degrees for crystalline erlose I. Plus 120.2 degrees for crystalline erlose II.

(6) Ultraviolet absorption spectrum: An aqueous solution of either crystalline erlose I or II exhibits no characteristic ultraviolet absorption.

(7) Infrared absorption spectrum: A transparent tablet prepared of a mixture of pulverulent crystalline erlose and dehydrated KBr was subjected to infrared spectrometry. An absorption spectrum as shown in FIG. 1 was obtained for crystalline erloses I and II.

(8) Solubility: One hundred ml of water dissolves 150 g of crystalline erlose I or 144 g of crystalline erlose II at 25° C.

(9) Appearance and properties: Crystalline erloses I and II are colorless, odorless, transparent crystals. Their microcrystals are white pulverulent solids. Approximately half the sweetening power of sucrose. On one-month standing, no hygroscopicity was noted.

Figure 2:
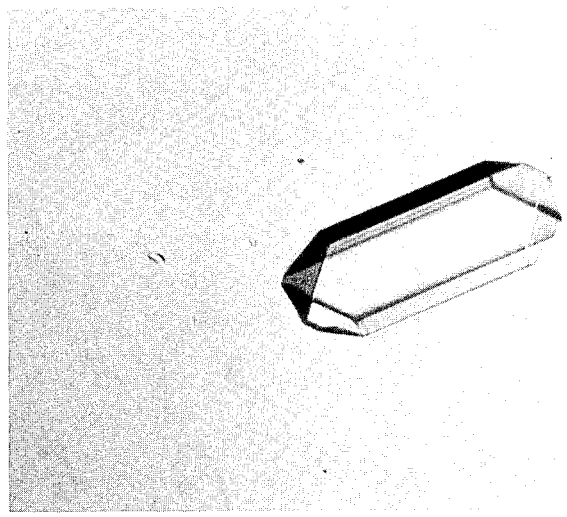
FIG. 2 is a photomicrographic view of crystalline erlose I.
Figure 3:
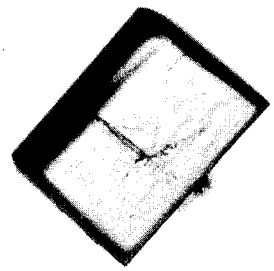
FIG. 3 is a photomicrographic view of crystalline erlose II.

Their aqueous solutions are neutral or slightly acidic. FIGS. 2 and 3 microphotographically show the crystallization of crystalline erloses I and II from an aqueous solution.

(10) Solubility in solvent: Crystalline erloses I and II are readily dissolvable in water, 0.1N NaOH, and 0.1N HCl; scarcely dissolvable in methanol, and ethanol; and insoluble in chloroform, and ethyl ether.

(11) Color reaction: Crystalline erloses I and II turn green by the anthronesulfuric acid reaction; turn red purple by the cysteinecarbazol reaction; and are negative to the Fehling's reduction reaction and the iodine reaction.

(12) Saccharide components (a) Paper- and gas-chromatographic analyses confirmed that the hydrolysate, obtained by hydrolyzing either crystalline erloses I or II with 1N sulfuric acid, consists of 2 moles of glucose and 1 mole of fructose. (b) On hydrolysis of a completely methylated crystalline erlose I or II, gas-chromatographic analysis of the hydrolysate revealed that crystalline erloses I and II consists of equimolar 2,3,4,6-tetra-O-methyl-D-glucose, 2,3,6-tri-O-methyl-D-glucose, and 1,3,4,6-tetra-O-methyl-D-fructose. (c) Crystalline erloses I and II are degraded into D-glucose and sucrose by α-glucosidase (EC 3.2.1.20) derived from *Mucor javanicus* microorganism; and into D-fructose and maltose by β-fructofuranosidase (EC 3.2.1.26) derived from a yeast.

Figure 4:
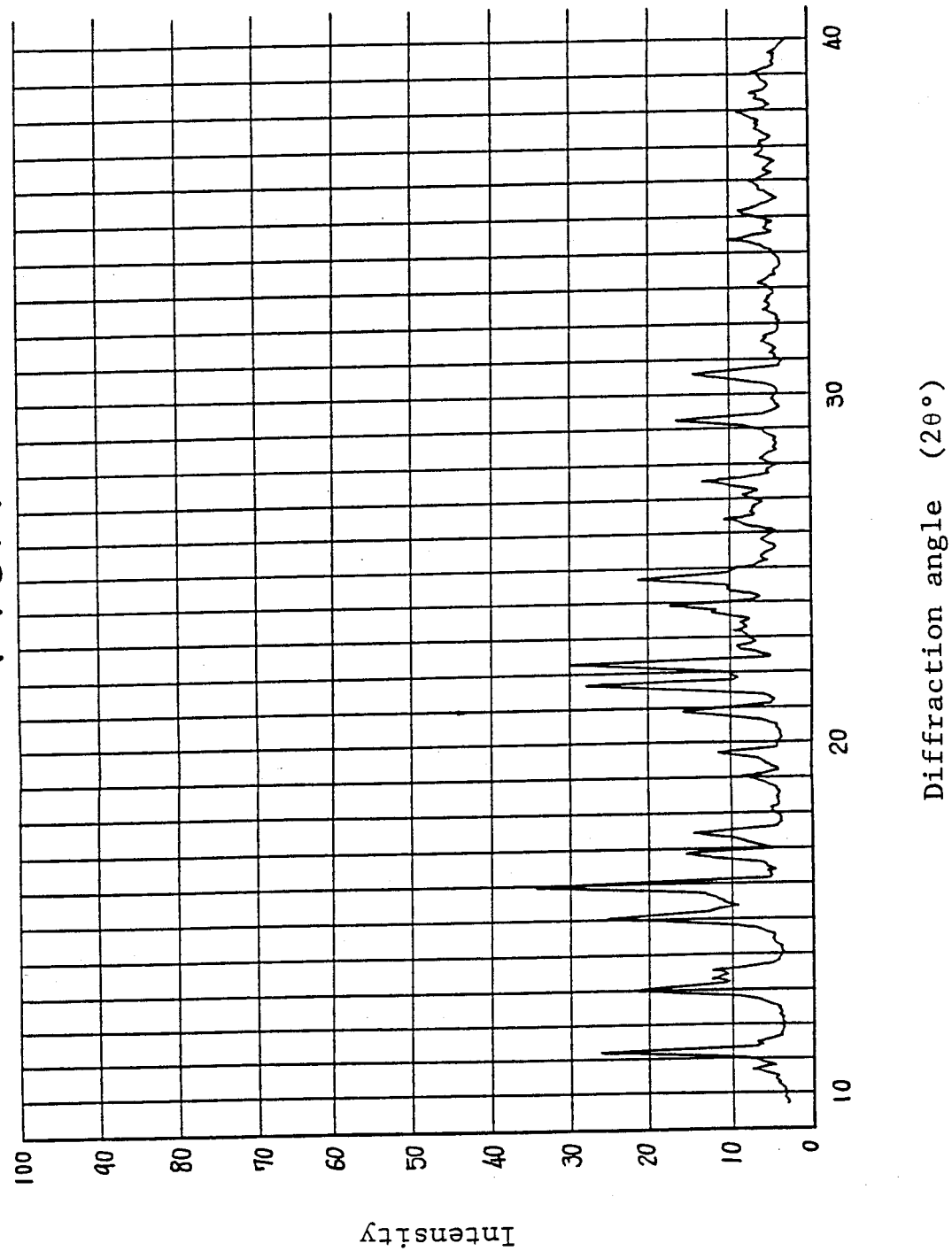
FIG. 4 is an x-ray diffraction figure of crystalline erlose I.

(13) x-Ray diffraction: x-Ray diffraction figures of crystalline erloses I and II were determined by the powder diffraction method as described by F. H. Stodola et al. in *Journal of the American Chemical Society*, Vol. 78, pp.2514–2518 (1956). The x-ray powder diffractometer employed was "GEIGERFREX RAD-II B" using CuKα ray, a product of Rigaku Corporation, Chiyoda-ku, Tokyo, Japan. The results are as shown in FIGS. 4 and 5. As the control, an x-ray diffraction figure of an amorphous pulverulent erlose, obtained by completely dissolving crystalline erlose I in hot water, and heat-drying the resultant solution, is as shown in FIG. 6. As is evident from these drawings, unlike the x-ray diffraction figure of the amorphous erlose, that of crystalline erlose I has predominant diffraction angles (2θ) of 11.2°, 15.1°, 15.9°, 21.7°, 22.3° and 24.7°, while that of crystalline erlose II has predominant diffraction angles (2θ) of 11.0°, 15.7°, 20.1°, 23.3° and 23.6°.

From these evidences, it is clear that the crystalline product according to the invention is a so far unknown non-hygroscopic crystalline erlose, more particularly, crystalline erlose hydrate.

The production of the crystalline erlose and mixture solid containing the same will hereinafter be described.

Although a small amount of erlose is found in certain natural products such as honey, a saccharide mixture solution that contains 10–35% erlose can be prepared in accordance with the enzymatic method as disclosed, for example, in Japan Patent Publication No. 40,949/74, Japan Patent Publication No. 17,660/78, Japan Patent Publication No. 22,520/81, and Japan Patent Kokai No. 47,929/77, wherein an aqueous solution containing either starch or a starch partial hydrolysate and sucrose is subjected to the action of either cyclomaltodextrin glucanotransferase (EC 2.4.1.19) or α-amylase (EC 3.2.1.1); another method as disclosed in Japan Patent Publication No. 58,950/82 wherin an aqueous solution containing either sucrose or raffinose and maltose is subjected to the action of levansucrase (EC 2.4.1.10); and still another method wherein an aqueous solution containing maltooligosaccharides, such as maltose, maltotriose and maltotetraose, and sucrose is subjected to the action of α-glucosidase (EC 3.2.1.20).

To prepare a crystallizable erlose solution, i.e. a high-purity erlose solution with an erlose content of 60% or higher, from such saccharide mixture solution, for example, fractionation methods such as membrane filtration method, fractional sedimentation method, liquid chromatography and column chromatography are feasible.

Conditions for crystalline erlose production are adequately selected according to the desired type of crystalline erlose. The requisite conditions are those that effect crystallization of erlose from a supersaturated erlose solution. More particularly, an erlose solution with a purity of 60% or higher is concentrated to about 55–95%, and the resultant syrup is adjusted to a temperature, for example, about 10°–70° C. for crystalline erlose I or about 40°–120° C. for crystalline erlose II. The temperature should be lower than the melting point of crystalline erlose to minimize the freezing, browning and degradation of the syrup.

To regulate the temperature and/or viscosity of the syrup, for example, methanol, ethanol or acetone may be added.

A supersaturated erlose solution, prewarmed to a relatively high temperature, is fed to a crystallizer, added with the seed in an amount of, desirably, about 0.1–20%, and gradually cooled while accelerating erlose crystallization by stirring.

In addition to a high-purity crystalline erlose, a mixture solid with a less crystalline erlose content can be used as the seed.

Examples of the procedures employed to prepare the resultant crystal suspension into crystalline erlose or a mixture solid containing the same include the conventional crystal separation-, block-pulverization-, fluidized-bed granulation-, and spray-drying-methods.

The crystal separation method usually contains the step of, for example, feeding the resultant crystal suspension to a basket-type centrifuge wherein the crystal suspension is separated into crystalline erlose and mother liquor. If necessary, the crystalline erlose can be easily washed by spraying it with a small amount of water to obtain a crystalline erlose of a much higher purity.

Since in the other three methods the mother liquor is not separated from the crystallized erlose, these methods do not lead to a product of a higher erlose purity, but to a higher yield. The pulverulent product, obtained by any of these methods, contains crystalline erlose, and, inevitably, small amounts of additional saccharides such as glucose, fructose, maltose, maltotriose, maltotetraose, sucrose, and maltosyl sucrose.

In the spray-drying method, a crystal suspension with a concentration of about 65–85%, crystallization of which has been effected up to about 25–60%, is spray-dried through a nozzle using a high-pressure pump, and the obtained pulverulent product is then dehydrated in a hot air stream at a temperature which does not melt the crystalline erlose. Subsequently, the pulverulent product is aged in a hot air stream for about one to twenty hours to obtain a non- or scarcely-hygroscopic mixture solid that contains the crystalline erlose.

In the block-pulverization method, generally a crystalline suspension with a moisture content of 5–25%, crystallization of which has been effected up to about 10–60%, is solidified into block by allowing it to stand for 0.1–5 days. A non-or scarcely-hygroscopic mixture solid containing the crystalline erlose is easily obtained by crushing and/or cutting the crystalline block, and dehydrating the resultant product.

The crystalline erlose and mixture solid containing the same thus obtained can be handled as sucrose because these products are both substantially non- or scarcely-hygroscopic, freely-flowing, wieldy, and free of caking or consolidation. Thus, these products can be favorably used to produce various orally-usable products, e.g. foodstuffs, cosmetics, dentifrices, pharmaceuticals, shaped articles, and chemicals.

The physicochemical properties of the crystalline erlose and mixture solid containing the same, e.g. melting point and specific rotatory power, vary dependent upon their erlose purity. Particularly, the melting point decreases and widens as the purity lowers. Thus, the erlose purity can be desirably selected to meet the final uses.

Furthermore, the crystalline erlose and mixture solid containing the same can be favorably used as a sweetener because, unlike sucrose, they readily dissolve in the mouth and endothermically absorb a large quantity of heat to provide a refreshing and pleasant taste.

In addition, the crystalline erlose and pulverulent solid containing the same can be favorably used to sweeten, in particular, pulverulent instant foodstuffs as described hereafter because these erlose products are substantially non- or scarcely-hygroscopic, while these erlose poducts are high in solubility and in dissolving rate in water. Thus, for example, pulverulent sweetener, shaped sweetener, fondant, chocolate, chewing gum, instant juice, instant soup, granule and tablet, can be easily prepared on an industrial-scale with these products.

The crystalline erlose and mixture solid containing the same are convenient to handle during, for example, packaging, transportation and storage because these erlose products are free-flowing due to their non-hygroscopicity and non-consolidating properties.

The crystalline erlose and mixture solid containing the same are highly water-soluble, heat-resistant, and low-cariogenic, as well as having sweetness-, body-, gloss- and viscosity-imparting properties. Thus, these erlose products can be freely used to prepard foodstuffs, cosmetics, dentifrices and pharmaceuticals wherein any of these is a requisite.

The properties and features of the erlose products according to the invention will be illustrated in more detail.

The crystalline erlose and mixture solid containing the same can be used intact as seasoning. The erlose products may be mixed with one or more of additional sweeteners, e.g. pulverulent starch sugar, glucose, isomerized sugar, sucrose, honey, maple sugar, sorbitol, maltitol, paratinose, dihydrocharcone, stevioside, α-glycosyl stevioside, sweet substance derived from *Momordica grosvenori* Swingle, glycyrrhizin, L-asparatyl L-phenylalanine methyl ester, saccharin, glycine, or alanine; and/or filler such as dextrin, starch or lactose.

The erlose products can be freely shaped, intact or after mixing with filler, vehicle and/or binder, into any desirable form, e.g. tablet, rod, plate, cube, etc.

The erlose products can be used as low-cariogenic sweetener because they are hardly fermentable by the cariogenic microorganism. The erlose products are suitable to sweeten low-cariogenic foodstuffs, e.g. confectioneries such as chewing gum, chocolate, biscuit, cookie, caramel, candy, and jelly; and beverages such as cola drinks, cider, juice, coffee, and those contain Lactobacillus microorganism, as well as to sweeten other orally-usable products such as cosmetics, dentifrices or pharmaceutical products directed to prevent dental caries.

The sweet taste of the erlose products well harmonize with sour-, salty-, astringent-, delicious- and/or bitter-tastes of the other ingredients, and the crystalline erlose per se is highly heat-resistant. Thus, in addition to the above mentioned special uses, the erlose products can be favorably used to sweeten foodstuffs in general or to improve the taste qualities thereof.

More particularly, the erlose products are freely usable to prepare seasonings, e.g. soy souce, powdered soy souce, miso, powdered miso, "moromi (an unrefined sake)", "hishio (a salted meat)", "furikake (a ground seasoned fish meal)", mayonnaise, dressing, vinegar, "sanbai-zu (a sauce of sake, soy, and vinegar)", "funmatsu-sushi-no-moto (a premix for seasoning sushi)", "chuka-no-moto (an instant mix of Chinese dish)", "tentsuyu (a sauce for Japanese deep-fat fried food)", "mentsuyu (a sauce for Japanese vermicelli)", sauce, catsup, "yakiniku-no-tare (a typical Japanese barbecue sauce)", curry roux, instant stew mix, instant soup mix, "dashi-no-moto (an instant stock mix)", mixed seasoning, "mirin (a sweetened sake used for cooking)", "shinmirin (a synthetic mirin)", table sugar, coffee sugar, etc., as well as to sweeten or improve the taste qualities of foodsuffs, e.g. Japanese-style confectioneries such as "senbei (a rice cracker)", "arare-mochi (rice-cake pellets)", "okoshi (a millet-and-rice cake)", rice paste, "manju (a bun with a bean-jam filling)", "uiro (a sweet rice jelly)", "an (a bean jam)", "yokan (a sweet jelly of beans)", "mizu-yokan (a soft adzuki-bean jelly)", "kingyoku (a kind of yokan)", jelly, pao de Castella (a sponge cake), and "amedama (toffees)"; confectioneries and bakery products such as bun, biscuit, cracker, cookie, pie, pudding, butter cream, custard cream, cream puff, waffle, sponge cake, doughnut, chocolate, chewing gum, caramel, and candy; frozen desserts such as ice cream, and shurbet; syrups such as "kajitsu-no-syrup-zuke (a preserved fruit)", and "kori-mitsu (a sugar syrup for shaved ice)"; pastes such as flour paste, peanut paste, fruit paste; processed fruits and vegetables such as jam, marmalade, and "syrup-zuke (fruit pickles)", "toka (a sugared fruit)"; pickles and pickled products such as "fukujin-zuke (red colored radish pickles)", "bettara-zuke (fresh radish pickles)", "senmaizuke (fresh radish pickles)", and pickled scallions; premixes for pickles and pickled products such as "takuan-zuke-no-moto (a premix for pickled radish)", and "hakusai-zuke-no-moto (a premix for fresh white rape pickles)"; meat products such as ham, and sausage; fish meat products such as fish ham, fish sausage, "kamaboko (a steamed fish paste)", "chikuwa (a kind of fish paste)", and "tenpura (a Japanese deep-fat fried food)"; "chinmi (relish)" such as "uni-no-shiokara (salted guts of sea urchin)", "ika-no-shiokara (salted guts of cuttlefish)", "su-konbu (a processed tangle)", "saki-surume (dried cuttlefish strips)", and "fugu-no-mirinboshi (a dried swellfish seasoned with mirin)"; "tsukudani (foods boiled down in soy)" such as those of laver, edible wild plants, dried cuttlefish, fish, and shellfish; daily dishes such as "nimame (cooked beans)", potato salad, and "konbu-maki (a tangle roll)"; milk products; canned and bottled products such as those of meat, fish meat, fruit, and vegetable; alcoholic beverages such as synthetic sake, and liquors; soft drinks such as coffee, cocoa, juice, carbonated beverage, sour milk beverage, and beverage containing a lactic bacterium; instant foodstuffs such as instant pudding mix, instant hot cake mix, juice powder, instant coffee, "sokuseki-shiruko (an instant mix of adzuki-bean soup with rice cake)", and instant soup mix.

The erlose products may be used for feeds and pet foods directed to domestic animal and fowl, pet animal, fish, honey bee, and silkworm.

In addition, the erlose products can be freely used to sweeten tobaccos, cosmetics, dentifrices and pharmaceuticals in solid, paste or liquid form, such as cigar, cigarette, dentifrice, lipstick, lipcream, medicine for internal administration, troche, cod-liver oil drop, oral refreshing agent, cachou, and collutorium, as well as to improve their taste qualities.

The erlose products can be, as in the case of sucrose, easily prepared into shaped sweeteners suitable for coffee and tea by spraying a small amount of water to the products to slightly moisten them, and molding the resultant material under slightly elevated pressure, for example, into shape of cube, fish or flower. The shaped sweeteners may be added with, for example, one or more sweeteners such as α-glycosyl stevioside, saccharin, or sucrose to increase the sweetness; edible coloring agent such as red or green; and/or flavor such as orange-, coffee- or brandy-flavor. The flavor can be used as an inclusion complex with cyclodextrin.

The crystalline erlose with a high erlose purity can be used in the form of a translucent or transparent non-hygroscopic sweetener, e.g. candy- or coffee-sugar, because such crystalline erlose can be easily recovered in massive form, e.g. crystalline sugar.

The crystalline erlose or a pulverulent mixture solid containing the same can be prepared, after mixing with one or more additional substances such as vitamin, antibiotic or Lactobacillus microorganism, into granule with a granulator, or into tablet with a tabletting machine.

The erlose products can be incorporated into the above mentioned foodstuffs, tobacco, pet foods, cosmetics, dentifrices, pharmaceuticals or shaped articles with conventional procedure before the completion of their processing. Examples of such procedures are mixing, kneading, dissolving, melting, immersing, permeating, sprinkling, applying, coating, spraying, injecting, crystallizing, and solidifying.

Several embodiments according to the invention will hereinafter be described.

EXAMPLE 1

Crystalline erlose

EXAMPLE 1-(1)

Preparation of cyclomaltodextrin glucanotransferase

A seed culture of *Bacillus stearothermophilus* FERM-P No.2222 was inoculated on 10 liters of a sterilized liquid culture medium comprising 2 w/v % soluble starch, 1 w/v % ammonium nitrate, 0.1 w/v % dipotassium phosphate, 0.05 w/v % magnesium sulfate heptahydrate, 0.5 w/v % corn steep liquor and 1 w/v % calcium carbonate, and cultured at 50° C. for three days under aeration-agitation conditions.

After centrifugation of the resultant culture, the supernatant was salted-out with ammonium sulfate at 0.7 saturation to obtain a crude enzyme specimen containing about 80,000 units of cyclomaltodextrin glucanotransferase (EC 2.4.1.19).

The one unit of cyclomaltodextrin glucanotransferase activity is defined as the amount of enzyme that diminishes completely the iodine-coloration of 15 mg soluble starch at 40° C. for 10 minutes under the following reaction conditions: To 5 ml of 0.3 w/w % soluble starch solution containing 0.02M acetate buffer (pH 5.5) and $2\times10^{-3}$M calcium chloride was added 0.2 ml of a diluted enzyme solution, and the mixture was incubated at 40° C. for 10 minutes. Thereafter, 0.5 ml of the reaction mixture was sampled, and added with 15 ml of 0.02N aqueous sulfuric acid solution to suspend the enzymatic reaction. The mixture was then added with 0.2 ml of 0.1N potassium iodide solution to effect coloration, and measured on the absorbance at a wavelength of 660 nm.

EXAMPLE 1-(2)

Preparation of saccharide mixture solution

An aqueous solution, prepared by dissolving 10 kg of β-cyclodextrin and 15 kg of sucrose in 200 liters of water, was added with a cyclomaltodextrin glucanotransferase, prepared by the method Example 1-(1), in an amount of 20 units/g β-cyclodextrin, and then reacted at pH 6.0 and 60° C. for forth hours.

The reaction mixture was heated, kept at 95° C. for fifteen minutes, cooled, concentrated to about 50%, and filtered. The filtrate was then purified by decoloring with activated carbon and deionizing with ion exchange resins in H- and OH-forms, and concentrated to obtain a mixture solution with a saccharide content of about 50% in a yield of about 93%. the saccharide mixture solution contained about 21% of erlose along with sucrose and maltodextrins.

EXAMPLE 1-(3)

Preparation of high-purity erlose solution

"Diaion SK102 ($Ca^{2+}$)", a strongly-acidic cation exchange resin in alkaline-earth metal form, degree of cross-linking, 2%, commercialized by Mitsubishi Chemical Industries ltd., Tokyo, Japan, was packed in an aqueous suspension in four jacketted stainless-steel columns, inside diameter, 5.4 cm, and the columns were cascaded to give a total bed depth of 20 m.

While keeping the inside column temperature at 55° C., the column was admitted first with a saccharide mixture solution, prepared by the method in Example 1-(2), in an amount of 5 v/v % to the resin, then with 55° C. water at a space velocity of 0.2, followed by sequential separation of the resultant effluents into the fraction rich in saccharide L; the fraction rich in saccharide L but highly contaminated with erlose; the fraction rich in erlose; the fraction rich in erlose but highly contaminated with saccharide S; and the fraction rich in saccharide S. Just before the elution of the saccharides was completed, the obtained fractions were successively recycled to the column, followed by admittance of a balancing amount of hot water. Upon five cycle repetitions of these operations, the effluents were sequentially separated into the fraction rich in saccharide L; the fraction rich in saccharide L but highly contaminated with erlose; the fraction rich in erlose; the fraction rich in erlose but highly contaminated with saccharide S; and the fraction rich in saccharide S. Thus, the fraction with an erlose content of about 95% was recovered in a yield of about 85% based on the saccharide mixture solution.

EXAMPLE 1-(4)

Preparation of crystalline erlose I seed

The high-purity erlose solution with an erlose purity of about 95%, obtained in Example 1-(3), was decolored with activated carbon, deionized with ion exchange resins in H- and OH-forms, and concentrated in vacuo to about 78% in usual way. A portion of the concentrate was then placed in a glass beaker, and allowed to stand at 10°–25° C. for about three months. Thus, crystalline erlose I was crystallized out. This crystalline product was crystalline erlose trihydrate, and used to seed in the following Example.

EXAMPLE 1-(5)

Production of crystalline erlose I

The high-purity crystalline erlose solution, concentration of about 78%, obtained in Example 1-(4), was added with the crystalline erlose I seed, obtained in Example 1-(4), and gradually cooled while accelerating erlose crystallization by gentle stirring. The resultant crystal suspension was separated by a basket-type centrifuge, and the crystals were washed by spraying a small amount of water to recover a high-purity crystalline erlose. An aqueous solution, prepared by dissolving the crystalline erlose in water while heating, was added with a small quantity of the seed, crystallized similarly as above, and separated to recover a crystalline erlose with a purity of over 99.8% (crystalline erlose I).

The crystalline erlose was the crystalline erlose hydrate with the afore-mentioned physiocochemical properties, and the yield was about 30% based on the saccharide mixture solution.

The product is wieldy, non-hygroscopic, and, therefore, suitable for a sweetener, in particularly, low-cariogenic sweetener, and also for a chemical and an intermediate of pharmaceutical compounds.

EXAMPLE 1-(6)

Preparation of crystalline erlose II seed

A crystalline erlose I, obtained by the method in Example 1-(5), was placed in a glass beaker, added with about 10 volumes of methanol, dissolved by heating, cooled by standing, and allowed to stand at ambient temperature for three days. Thus, crystalline erlose II was crystallized out, and used as the seed in the following Example. The product was crystalline erlose monohydrate.

EXAMPLE 1-(7)

Production of crystalline erlose II

A crystalline erlose I, obtained by the method in Example 1-(5), was placed in a stainless-steel vessel, and melted by heating. The melted specimen was added with the seed, obtained in Example 1-(6), mixed with stirring, transferred into an aluminium tray, and crystallized into block by about 4-hour standing at about 70° C. The block was fed to a pulverizer, and then dehydrated in an air stream at ambient temperature for about five hours to obtain a crystalline erlose (crystalline erlose II).

The crystalline erlose was crystalne erlose hydrate with the afore-mentioned physicochemical properties, and the yield was about 90% based on the crystalline erlose I.

The product is wieldy, non-hygroscopic, and, therefore, suitable for a sweetener, in particular, low-cariogenic sweetener, and also for a chemical and an intermediate of pharmaceutical compounds.

EXAMPLE 2

Pulverulent mixture solid containing crystalline erlose

EXAMPLE 2-(1)

Preparation of levansucrase

Sixty liters of a liquid culture medium consisting of 3 w/v % defatted soybean, 2 w/v % glucose, 4 w/v % sucrose, 0.6 w/v % diammonium phosphate, 0.03 w/v % magnesium sulfate heptahydrate, 0.02 w/v % potassium chloride, 0.02 w/v % calcium acetate, 0.001 w/v % manganese sulfate tetrahydrate and tap water was adjusted to pH 7.0, and sterilized by heating at 120° C. for twenty minutes. A seed culture of *Bacillus subtilis* ATCC 6051 was then inoculated on the liquid culture medium, and cultured at 37° C. for three days under aeration-agitation conditions.

The supernatant, obtained by centrifuging the resultant culture, was added with equi-volume of cold ethanol, and the resultant sediment was recovered and dissolved in 20 mM acetate buffer (pH 5.0) containing 1 mM calcium chloride. The solution was then dialyzed against a fresh acetate buffer of the same composition overnight, followed by centrifugation. The resultant supernatant was passed through a column of DEAE-cellulose to adsorb the levansucrase which was then eluted with a fresh acetate buffer of the same composition. The resultant elute was added with ammonium sulfate to give 90% saturation. The resultant sediment was recovered, and dissolved in 500 ml of a fresh acetate buffer of the same composition. The activity of the levansucrase solution was about 120 units/ml.

The activity of levansucrase was assayed as follows: Two ml of a mixture solution containing 10 w/v % sucrose, 50 mM phosphate buffer (pH 7.0) and levansucrase was kept at 30° C. for thirty minutes. The levansucrase was then heat-inactivated, and the liberated glucose was determined by the glucoseoxidase method. The one unit of levansucrase is defined as the amount of enzyme that liberates 1 micromole of glucose under these conditions.

EXAMPLE 2-(2)

Preparation of saccharide mixture solution

An aqueous solution containing 10% of sucrose and 40% of maltose was added with a levansucrase, prepared by the method in Example 2-(1), in an amount of 2 units/g sucrose, and reacted at 35° C. and pH 5.5 for forty hours. The reaction mixture was then purified, and concentrated similarly as in Example 1-(2) to obtain a 60% saccharide mixture solution in a yield of 95%.

The saccharide mixture solution contained about 20% of erlose along with about 4% of saccharide L and about 76% of saccharide S.

EXAMPLE 2-(3)

Preparation of high-purity erlose solution

The saccharide mixture solution, obtained in Example 2-(2), was fractionated similarly as in Example 1-(3) to obtain the fraction with an erlose purity of 90% in a yield of about 92% based on the saccharide mixture solution, except that "Dowex 50WX4 (Mg$^{2+}$)", a strongly-acidic cation exchange resin in alkaline-earth metal form, degree of cross-linking, 4%, commercialized by Dow Chemicals Co., Midland, Mich., USA, was chosen and used to increase the erlose purity of the saccharide mixture solution.

EXAMPLE 2-(4)

Production of mixture solid containing crystalline erlose

The high-purity erlose solution, obtained in Example 2-(3), was purified similarly as in Example 1-(4), concentrated in vacuo to about 80%, seeded with 2% of a crystalline erlose I, prepared by the method in Example 1-(5), and gradually cooled from 60° C. while gently stirring. The crystal suspension, crystallization of which had been effected up to about 35%, was sprayed through a 1.5 mm nozzle, equipped at the top of a spraying tower, under 150 kg/cm$^2$ produced with a high-pressure pump. Simultaneously, 60° C. air was passed from the top of the tower onto a net conveyer carrying a fluidized crystalline erlose as the seed. The conveyer was placed at the bottom of the tower to collect the pulverulent product on the net conveyer and also to fluidize the product out of the tower over a period of forty minutes while passing a stream of 40° C. air upwards through the net. The pulverulent crystalline product was then placed in an ageing tower and aged for about eight hours to obtain a pulverulent mixture solid containing crystalline erlose in a yield of about 85% based on the erlose constituent in the saccharide mixture solution.

The pulverulent product is wiedly, non-hygroscopic, and, therefore, suitable for a sweetener, in particular, low-cariogenic sweetener, directed to prepare foodstuffs, cosmetics, detifrices and pharmaceuticals.

EXAMPLE 2-(5)

Production of mixture solid containing crystalline erlose

A mixture solid containing crystalline erlose, obtained by the method in Example 2-(4), was placed in a crystallizer, melted by heating to 90° C., seeded with 1% of a crystalline erlose obtained by the method in Example 1-(7), mixed by stirring, poured into an aluminium tray, and crystallized into block by 10-hour standing at about 55° C. The block was then pulverized with a pulverizer, and dehydrated in a stream of a hot air for about twenty minutes to obtain a pulverulent mixture solid containing crystalline erlose.

The pulverulent mixture solid is wieldy, non-hygroscopic, and, therefore, suitable for a sweetener, in particular, low-cariogenic sweetener, directed to prepare foodstuffs, cosmetics, dentifrices and pharmaceuticals.

EXAMPLE 3

Fondant

A high-purity erlose solution, obtained by the method in Example 2, was concentrated to 85%, placed in a crystallizer, seeded with 5% of a crystalline erlose obtained by the method in Example 2-(4), cooled to ambient temperature under vigorous stirring, and mixed with a crystalline erlose obtained by the method in Example 1-(5) to obtain a fondant.

The resultant white, smooth, and mildly sweet paste product is favorably usable to prepare confectioneries.

EXAMPLE 4

Sweetener

A pulverulent sweetener obtained by admixing 1 part of a pulverulent mixture solid containing crystalline erlose, obtained by the method in Example 2-(4), with 0.05 parts of "α-G-Sweet", an α-glycosyl stevioside commercialized by Toyo Sugar Refining Co., Ltd., Tokyo, Japan, had an excellent sweetness which was about two-fold higher in sweetening power than that of sucrose, but having a calorific value about half of that of sucrose.

The sweetener is thus suitable for use in various low-calorific foodstuffs for diabetics, obeses and those whose calory-intakes are restricted.

The sweetener is favorably usable for sweetening foodstuffs directed to suppress dental caries because cariogenic microorganism scarcely forms acid and insoluble glucan from the sweetener.

EXAMPLE 5

Cubic sweetener

One part of a crystalline erlose, obtained by the method in Example 1-(5), was admixed with 0.01 part of saccharin, moistened by spraying a small amount of an aqueous pullulan solution, formed into cubes with a mold for cubic sugar under a relatively high pressure, and removed from the mold to obtain a cubic sweetener.

The product is a white, non-hygroscopic sweetener with a sufficient physical strength and about two-fold higher sweetening power than sucrose, as well as being readily dissolvable in cold water.

The product has low-calorific and low-cariogenic properties.

EXAMPLE 6

Cream wafers

A creamy product, obtained by admixing 2,000 parts of a pulverulent mixture solid containing crystalline erlose obtained by the method in Example 2-(4), 1,000 parts of shortening. 1 part of lecithin, 1 part of lemon oil, and 1 part of vanilla oil in usual way, was kept at 40°-45° C., and sandwitched between wafers to obtain cream wafers.

EXAMPLE 7

Custard cream

Five hundred parts of cornstarch, 500 parts of a pulverulent mixture solid containing crystalline erlose obtained by the method in Example 2-(5), 400 parts of maltose, and 5 parts of kitchen salt were mixed by shifting and sieving, added with 1,400 part of egg, stirred, gradually added with boiling milk, and heated on a slow fire while stirring. The heating was stopped when the cornstarch gelatinized and the mixture became translucent. The mixture was then cooled, and added with a small amount of vanilla flavor to obtain a custard cream.

The product is a smooth, glossy and tasty custard cream with no excessive sweetness.

EXAMPLE 8

Chocolate

Forty parts of cacao paste, 10 parts of cacao butter, and 50 parts of a crystalline erlose obtained by the method in Example 1-(7) were mixed, and fed to a refiner to reduce the particle size, transferred into a conche, and kneaded at 50° C. for two days. Half part of lecithin was added and homogenously dispersed during the the step of kneading.

The mixture was adjusted to 31° C. with a thermoregulator, poured into a mold just before the cacao butter solidified, deaerated with a vibrator, solidified by passing it through a 10° C. cooling tunnel over a period of twenty minutes, and removed from the mold to obtain a product.

The product is free of hygroscopicity, excellent in color, gloss, flavor and texture, and smoothly melts to provide a mild sweetness.

The product is suitable for low-cariogenic chocolate.

EXAMPLE 9

Chocolated-coated candy

Ninety-five parts of a pulverulent mixture solid containing crystalline erlose obtained by the method in Example 2-(4), 5 parts of corn syrup, and small amount of water were mixed into fluid while stirring, added with small amounts of flavor and coloring, poured with a depositor into a mold of layered starch, partially solidified in the mold, and separated from the starch by shifting and sieving the starch to obtain centers for chocolate-coated candy.

The centers were coated with a chocolate, obtained by the method in Example 8, solidified by cooling, and packaged to obtain the captioned product.

EXAMPLE 10

Chewing gum

Twenty-five parts of gum base and forty parts of a fondant, obtained by the method in Example 3, were kneaded with a mixer at 60° C., mixed with 30 parts of a crystalline erlose obtained by the method in Example 1-(7), 1.5 parts of calcium phosphate and 0.1 part of an inclusion compound of L-menthol and $\beta$-cyclodextrin, further mixed with a small amount of seasoning, sufficiently kneaded, rolled out, and cut into strips.

The product is suitable for low-cariogenic chewing gum.

EXAMPLE 11

Instant corn potage soup

Thirty parts of gelatinized pulverulent corn, 5 parts of gelatinized pulverulent flour, 4 parts of gelatinized potato starch, 12 parts of gelatinized waxy cornstarch, 8 parts of a pulverulent mixture solid containing crystalline erlose obtained by the method in Example 2-(5), 5 parts of sodium glutamate, 8.5 parts of cooking salt, 7 parts of defatted milk, and 0.5 parts of onion powder were pulverized, homogenously mixed, admixed with 0.5 parts of sorbitan fatty acid ester and 9 parts of a heat-melted hardened vegetable oil, further admixed with 10 parts of lactose, fed to a fluidized-bed granulator, exhaustion temperature of 40° C., airflow of 150 m$^2$/min, sprayed and coated with 5% pullulan solution at a rate of 100 ml/min, and granulated for thirty minutes to obtain a product.

Addition of hot water immediately dissolves and disperses the product to give a tasty soup.

EXAMPLE 12

"Uiro-no-moto (premix for sweet rice jelly)"

Ninety parts of pulverulent rice was admixed with 20 parts of cornstarch, 120 parts of a pulverulent mixture solid containing crystalline erlose obtained by the method in Example 2-(4), and 4 parts of pullulan to obtain "uiro-no-moto".

Two hundred g of "uiro-no-moto" and 1 g of "matcha (ground tea)" were added with water, kneaded, placed in a vessel, and steamed for sixty minutes to obtain "matcha-uiro (ground tea-flavored uiro)".

The product is excellent in gloss, texture and flavor, and stable over a low period of time because retrogradation of the amylaceous ingredient is suppressed.

EXAMPLE 13

"Bettara-zuke-no-moto (premix-type seasoning for fresh radish pickles)"

Four parts of a pulverulent mixture solid containing crystalline erlose obtained by the method in Example 2-(5), 0.05 parts of a licorice extract, 0.008 parts of malic acid, 0.07 parts of sodium glutamate, 0.03 parts of potassium sorbate, and 0.2 parts of pullulan were homogenously mixed to obtain "bettara-zuke-no-moto".

Thirty kg of fresh radish was first pickled with cooking salt, then with sucrose in conventional manner. Thereafter, the radish was further pickled in a seasoning solution prepared with 4 kg of "bettara-zuke-no-moto" to obtain "bettara-zuke".

The product was crisp, mildly sweet, and excellent in color, gloss and flavor.

EXAMPLE 14

Tablet

Fifty parts of salicylic acid, 9 parts of a crystalline erlose obtained by the method in Example 1-(7), 5 parts of maltose, and 4 parts of cornstarch were mixed to homogeneity, tabletted with a tabletting machine to obtain 5.25 mm and 680 mg tablets.

The product is free of hygroscopicity, sufficient in physical strength, and satisfactory in water-degradability.

EXAMPLE 15

Fatty acid ester of erlose

Two parts of a crystalline erlose, obtained by the method in Example 1-(5), was dehydrated in vacuo to an anhydrous state, dissolved in 7 parts of dimethylformamide, and mixed with 0.6 parts of methyl palmitate and 0.04 parts of potassium carbonate. The resultant solution was reacted overnight while stirring at about 80°–100° C. under 100–200 mmHg. After completion of the reaction, the solvent was removed, and the residue was immersed twice in three volume aliquots of acetone. The exudate was then concentrated, and washed sequentially with benzene and petroleum ether, after which the resultant viscous oily product was immersed in three parts of acetone. The sediment, formed by allowing the exudate to stand under ice-chilling conditions, was treated with acetone, and dehydrated to obtain 0.6 parts of erlose monopalmitate.

The product is favorably usable to prepare detergent and food-grade emulsifier because the product is excellent in surface activity.

As many apparently widely different embodiments of this invention may be made without departing from the spirit and scope thereof, it is to be understood that the invention is not limited to the specific embodiments thereof except as defined in the appended claims.

We claim:

1. A crystalline erlose hydrate, which gives predominant diffraction angles ($2\theta$) of 11.2°, 15.1°, 15.9°, 21.7°, 22.3°, and 24.7° upon x-ray powder diffraction analysis with CuK$\alpha$ ray.

2. A crystalline erlose, which gives predominant diffraction angles ($2\theta$) of 11.0°, 11.7°, 20.1°, 21.0°, 23.3°, and 23.6° upon x-ray powder diffraction analysis with CuK$\alpha$ ray.

3. A process for producing a crystalline erlose hydrate, comprising:

providing a first erlose solution having an erlose content of at least 60%, solute concentration in the range of 55 to 95% by weight, and temperature in the range of 10° to 120° C.;

adding 0.1 to 20% by weight of seed crystals of an erlose hydrate giving predominate diffraction angles ($2\theta$) of 11.2°, 15.1°, 15.9°, 21.7°, 22.3°, and 24.7° upon X-ray powder diffraction analysis using CuK$\alpha$ ray (crystalline erlose hydrate I) to the solution; and maintaining the resultant mixture at a temperature below the melting point of the crystalline erlose hydrate I to crystallize erlose hydrate I from said mixture.

4. A process for producing a crystalline erlose hydrate, comprising:

providing a first erlose solution having an erlose content of at least 60%, solute concentration in the range of 55 to 95% by weight, and temperature in the range of 10° to 120° C.;

adding 0.1 to 20% by weight of seed crystals of an erlose hydrate giving predominant diffraction angles ($2\theta$) of 11.0°, 15.7°, 20.1°, 21.0°, 23.3°, and 23.6° upon X-ray powder diffraction analysis using CuK$\alpha$ ray (crystalline erlose hydrate II) to the solution, and maintaining the resultant mixture at a temperature below the melting point of the crystalline erlose hydrate II to crystallize erlose hydrate II from said mixture.

* * * * *

UNITED STATES PATENT AND TRADEMARK OFFICE
CERTIFICATE OF CORRECTION

PATENT NO. : 4,758,660
DATED : July 19, 1988
INVENTOR(S) : Takeuchi et al.

It is certified that error appears in the above-identified patent and that said Letters Patent is hereby corrected as shown below: On the title page Correct the name of assignee as follows:

[73] Assignee: Kabushiki Kaisha Hayashibara Seibutsu Kagaku Kenkyujo, Okayama, Japan Signed and Sealed this Twentieth Day of June, 1989

Attest:

DONALD J. QUIGG

Attesting Officer

Commissioner of Patents and Trademarks